US011280792B2

(12) United States Patent
Takeda et al.

(10) Patent No.: US 11,280,792 B2
(45) Date of Patent: Mar. 22, 2022

(54) APPARATUS FOR DETECTING THE DEGREE OF MALIGNANCY OF EACH OF CIRCULATING TUMOR CELLS

(71) Applicants: ON-CHIP BIOTECHNOLOGIES CO., LTD., Tokyo (JP); SHIZUOKA PREFECTURE, Shizuoka (JP)

(72) Inventors: Kazuo Takeda, Tokyo (JP); Namiko Yamashita, Tokyo (JP); Yuu Fujimura, Tokyo (JP); Kaori Nishio, Tokyo (JP); Yasuhiro Koh, Shizuoka (JP); Masaru Watanabe, Shizuoka (JP); Fumiaki Koizumi, Tokyo (JP); Yuri Uehara, Tokyo (JP)

(73) Assignees: ON-CHIP BIOTECHNOLOGIES CO., LTD., Tokyo (JP); SHIZUOKA PREFECTURE, Shizuoka (JP)

( * ) Notice: Subject to any disclaimer, the term of this patent is extended or adjusted under 35 U.S.C. 154(b) by 411 days.

(21) Appl. No.: 16/123,444

(22) Filed: Sep. 6, 2018

(65) Prior Publication Data

US 2019/0011450 A1 Jan. 10, 2019

Related U.S. Application Data

(62) Division of application No. 14/388,445, filed as application No. PCT/JP2013/059202 on Mar. 28, 2013, now abandoned.

(30) Foreign Application Priority Data

Mar. 28, 2012 (JP) ................................ 2012-074030

(51) Int. Cl.
*G01N 33/574* (2006.01)
*C12N 5/09* (2010.01)
*G01N 33/58* (2006.01)

(52) U.S. Cl.
CPC ..... *G01N 33/57492* (2013.01); *C12N 5/0693* (2013.01); *G01N 33/574* (2013.01); *G01N 33/58* (2013.01); *G01N 33/582* (2013.01)

(58) Field of Classification Search
CPC ........... G01N 33/57492; G01N 33/574; G01N 33/58; G01N 33/582; C12N 5/0693
See application file for complete search history.

(56) References Cited

U.S. PATENT DOCUMENTS

| 2002/0172987 A1 | 11/2002 | Terstappen et al. |
| 2006/0211060 A1 | 9/2006 | Haley et al. |

(Continued)

FOREIGN PATENT DOCUMENTS

| JP | 2006029921 A | 2/2006 |
| JP | 2007178193 A | 7/2007 |

(Continued)

OTHER PUBLICATIONS

Lecharpentier et al. Detection of circulating tumour cells with a hybrid (epithelial/mesenchymal) phenotype in patients with metastatic non-small cell lung cancer. British Journal of Cancer 105: 1338-1341 (Oct. 4, 2011)—IDS.*

(Continued)

*Primary Examiner* — Gailene Gabel
(74) *Attorney, Agent, or Firm* — Heslin Rothenberg Farley & Mesiti P.C.

(57) ABSTRACT

The object of the present invention is to provide an evaluation method capable of accurately determining a metastasis of cancer, the stage of cancer progression, or the malignancy of cancer.
The object can be solved by a method for detecting the degree of malignancy of each of the circulating tumor cells, characterized by the following steps: (a) bringing an epithelial cell-binding component, which specifically binds to a (Continued)

marker molecule expressed on epithelial cells and is fluorescently-labeled or luminescent enzyme-labeled, and a mesenchymal cell-binding component, which specifically binds to a marker molecule expressed on mesenchymal cells and is fluorescently-labeled or luminescent enzyme-labeled, into contact with a sample that possibly contains circulating tumor cells, (b) detecting a fluorescence signal or a luminescence signal of the epithelial cell-binding component and a fluorescence signal or a luminescence signal of the mesenchymal cell-binding component of each of the cells, and (c) determining the degree of epithelial-mesenchymal transition of circulating tumor cells based on the signal amount of the epithelial cell-binding component (E) and the signal amount of the mesenchymal cell-binding component (M).

5 Claims, 4 Drawing Sheets (56) References Cited

U.S. PATENT DOCUMENTS

| | | |
|---|---|---|
| 2006/0254972 A1 | 11/2006 | Tai et al. |
| 2007/0026469 A1 | 2/2007 | Fuchs et al. |
| 2008/0069300 A1 | 3/2008 | Saito |
| 2009/0258365 A1 | 10/2009 | Terstappen et al. |
| 2011/0294139 A1 | 12/2011 | Takeda |
| 2011/0312511 A1 | 12/2011 | Winquist et al. |
| 2012/0288920 A1 | 11/2012 | Takeda |
| 2012/0302572 A1 | 11/2012 | Kan et al. |
| 2013/0302828 A1* | 11/2013 | Takeda ............ G01N 33/57492 435/7.23 |

FOREIGN PATENT DOCUMENTS

| | | |
|---|---|---|
| JP | 2008533490 A | 8/2008 |
| JP | 2010014416 A | 1/2010 |
| JP | 2010181349 A | 8/2010 |
| JP | 2011503520 A | 1/2011 |
| JP | 2011515109 A | 5/2011 |
| WO | 2008104380 A2 | 9/2008 |
| WO | 2009120767 A1 | 10/2009 |
| WO | 2011086990 A1 | 7/2011 |

OTHER PUBLICATIONS

Pelosi et al. Epithelial-Mesenchymal Transition: From diagnosis to therapy. Journal of Thoracic Oncology 6 (6): Suppl. 2 (Jun. 2011).*
Extended European Search Report issued in connection with application EP 18193730 dated Nov. 13, 2018.
Kawai et al., Effect of Bromoindirubin-3-oxime on human deciduous tooth dental pulp cells, Shika Yakubutsu Ryoho—Oral Therapeutics and Pharmacology, Shika Yakubutsu Ryoho Kenkyukai, Tokyo, JP, v.31, No. 3, Jan. 1, 2012, 87-95.
Min et al., High Expression of Snail mRNA in Blood from Hepatocellular Carcinoma Patients with Extra-Hepatic Metastasis, Clinical end Experimental Metastasis; Official Journal of the Metastasis Research Society, Kluwer Academic Publisher, DO, vol. 26, No. 7, Jun. 16, 2009, 1573-7276.
Magbanua et al., P4-07-17: Isolation of highly pure circulating tumor cells (CTCs) from metastatic breast cancer (MBC) patients for gene expression analysis, Cancer Research, vol. 71, No. 24, Supplement, Dec. 15, 2011, P4-07-17-P4-07-17, 102nd Annual Meeting of the American-Association-for-Cancer-Research (AACR); Orlando, FL, USA, Apr. 2-6, 2011.
International Search Report for PCT/JP2013/059202 dated May 7, 2013.
Kallergi G et al; "Epithelial-Mesenchymal Transition Markers Are Expressed in CTCS of Breast Cancer Patients," Ann Oncol, 2009, vol. 20, No. Supplement 2, p. II56 170P.
Kiyotsugu Yoshikawa; "Stemness and epithelial-mesenchymal transition in breast cancer," Saishin Igaku, 2010, vol. 65, 6 gatsu special extra issue, pp. 1331-1342.
Gianni et al; "Circulating Tumor Cells in Colorectal Cancer: A Comparison Between Young and Elderly Patients," Ann Oncol, 2011, vol. 22, No. Supplement 5, p. V111 P-0327.
Shintani et al; "Haigan Hoshasen Kagaku Ryohogo no Setsujo Hyohon ni Okeru Johi Kan'yo Tenkan EMT Marker no Kento," Japanese Journal of Lung Cancer, 2010, vol. 50, No. 5, p. 510, O-59.
Ksiazkiewicz et al; "Epithelial-Mesenchymal Transition: A Hallmark in Metastasis Formation Linking Circulating Tumor Cells and Cancer Stem Cells," Pathobiology, Apr. 4, 2012, vol. 79, No. 4, pp. 195-208.
Kojima et al; "A simple biological imaging system for detecting viable human circulating tumor cells," The Journal of Clinical Investigation, 2009, vol. 119, p. 3172-3181.
Kallergi et al; "Epithelial to mesenchymal transition markers expressed in circulating tumour cells of early and metastatic breast cancer patients," Breast Cancer Research (Great Britain), 2011, vol. 13, R59.
Micalizzi et al; "Epithelial-Mesenchymal Transition in Cancer: Parallels Between Normal Development and Tumor Progression," Journal of Mammary Gland Biology and Neoplasia (Germany), 2010, vol. 15, p. 117-134.
Lyons et al; "Axillary node staging for microinvasive breast cancer: Is it justified?" Journal of Clinical Oncology, 2011, vol. 29.
CytoTrack Poster, 2009, http://ing.dk/modules/fsArticle/download.php?fileid=550.
Takao et al; Enumeration, Characterization, and Collection of Intact Circulating Tumor Cells by Cross-Contamination-Free Flow Cytometry, Cytometry Part A, 2011, vol. 79A, p. 1047-117.
Avri Ben Ze'ev; "Differential Control of Cytokeratins and Vimentin Synthesis by Cell-Cell Contact and Cell Spreading in Cultured Ephithelial Cells," The Journal of Cell Biology, 1984, vol. 99, p. 1424-1433.
Lecharpentier, et al., "Detection of circulating tumour cells with a hybrid (epithelial/mesenchymal) phenotype in patients with metastatic non-small cell lung cancer," British Journal of Cancer (2011) 105, 1338-1341.
Rhim, et al., "EMT and dissemination precede pancreatic tumor formation, NIH Public Access Author Manuscript," Cell, Jan. 20, 2012, 148(1-2): 349-361.
Supplementary Partial European Search Report for EP 13770163 dated Nov. 5, 2015.
Perez et al. "Simultaneous measurement of multiple activity kinase states using polychromatic flow cytometry", Nature, 2002, 20:155-162.

* cited by examiner

APPARATUS FOR DETECTING THE DEGREE OF MALIGNANCY OF EACH OF CIRCULATING TUMOR CELLS

CROSS REFERENCE TO RELATED APPLICATION

This application is a divisional of U.S. patent application Ser. No. 14/388,445, filed on Sep. 26, 2014, now abandoned as a National Phase filing under 35 U.S.C. § 371 of PCT International Application No. PCT/JP2013/059202, filed Mar. 28, 2013, and published under PCT Article 21(2) in Japanese as WO 2013/146993 on Oct. 3, 2013, which claims priority to Japanese Application No. 2012-074030, filed Mar. 28, 2012. The contents of each of the foregoing applications are incorporated by reference herein in their entireties.

TECHNICAL FIELD

The present invention relates to a method for detecting the degree of malignancy of each of the circulating tumor cells, a kit for detecting the degree of malignancy of the circulating tumor cells, and an apparatus for detecting the degree of malignancy of the circulating tumor cells.

BACKGROUND ART

Recently, it has become important to select an effective anticancer drug for each cancer patient by removing cancer cells from the cancer patient, and diagnosing the cancer cells thoroughly, for example, a molecular biological analysis such as gene variation analysis. It is known that extremely-low concentrated cancer cells can be detected in the blood of the cancer patients. These cancer cells are referred to as circulating tumor cell (hereinafter sometimes referred to as CTC). The number of the detected CTC is correlated to a prognosis of the patient. Therefore, a measurement of CTC begins to be performed, so as to evaluate a stage of cancer progression.

When CTCs are detected in the peripheral blood of cancer patients, extremely-low concentrated CTCs which are one-billionth of high concentrated blood cells, should be detected in the high concentrated blood cells. Thus, a count loss of CTCs or a contamination between samples of patients leads to a seriously wrong diagnosis. For example, the measurement of CTCs is carried out using CellSearch System (U.S.A). As disclosed in Patent reference 1, in the above technique, the cells are subjected to nuclear staining and cytokeratin staining, and then the cells are reacted with CD326 antibody-immobilized magnetic beads. The resulting cells are then allowed to float through a magnetic field. Fluorescent imaging of cells are obtained by scanning by laser beam and then a human determines whether or not each of the cells is CTC, on the basis of the fluorescent imaging. Further, there is a technique called CTC-Chip as a method for measuring CTCs. As disclosed in Patent reference 2, in the above technique, a blood sample is passed through a chip in which 80,000 micro posts are formed on a silicon wafer about the size of a business card. Then, all of the 80,000 micro posts immobilized with anti-EpCAM antibody are image-recognized so as to identify and measure CTCs. Patent reference 3 discloses that CTCs detected by the method disclosed in Patent reference 1, are recovered, and then genes of the recovered CTCs are analyzed by fluorescence in situ hybridization (hereinafter sometimes referred to as FISH). Patent reference 4 and 9 discloses a flowcy-tometer using a disposable chip. A measurement without a cross contamination of samples can be conducted with the above flowcytometer. Patent reference 5 discloses a conventional flow cytometer wherein a solution sending system including a flow cell is fixed. Patent reference 6 discloses that CTCs detected by the method disclosed in Patent reference 1, are recovered, and then an abnormality of IGF-1R gene of CTCs is analyzed by FISH. Patent reference 8 discloses that CTCs are concentrated by a microfilter on the basis of cell size. Non-patent reference 1 discloses that a fluorescent protein i.e. GFP is expressed in cancer cells by using a virus capable of infecting cancer cells only, and the expressed cell is detected by a fluorescence microscope. Non-patent reference 1 discloses that when an epithelial-mesenchymal transition (hereinafter sometimes referred to as EMT) in cancer cells derived from an epithelial cell is induced, the cancer cells easily become detached and easily migrate to other regions. The EMT is proposed by Elizabeth Hay et al. in the early 1980's. In the EMT, the epithelial cell is morphologically altered to a mesenchymal-like cell. Further, Non-patent reference 1 discloses that a degree of EMT is related to a metastasis of cancer. Non-patent reference 2 discloses that an EMT is induced in CTC derived from epithelial cell also. Non-patent reference 7 discloses findings on EMT of culture cells by protein analysis using an electrophoresis. It is reported that a ratio between an expression amount of cytokeratin and an expression amount of vimentin is not altered, but constant during the cell cycle. The ratio between expressions is measured by data of electrophoresis, and therefore the ratio is the average of a number of cells.

In Non-patent reference 4, a method for separating CTCs derived from prostate cancer from leucocytes and concentrating CTCs by means of CPT Vacutainer tubes manufactured by Becton, Dickinson and Company is disclosed. Non-patent reference 5 discloses a CYTOTRACK system manufactured by CYTOTRACK (U.S.A). The CYTOTRACK system does not comprise a specific concentration step before detection. That is to say, cells containing CTCs are separately fixed on a disc after labelling with a fluorescent antibody. Consequently, the CTCs on the disc are detected by laser-scanning using a compact disc turntable system. In Non-patent reference 6, a method for magnetically-concentrating CTCs using an anti-EpCAM antibody, and a method for detecting CTCs using the apparatus disclosed in Patent reference 4, are disclosed.

Further, as a reagent kit relevant to CTCs, there may be mentioned a basic research reagent kit for magnetically-concentrating CTCs from peripheral blood (D326(EpCAM) Tumor Cell Enrichment and Detection Kit; Miltenyi Biotec, catalog number 130-090-500); a reagent kit for magnetically-concentrating epithelial cells (HUMAN EpCAM POSITIVE SELECTION KIT; STEMCELL Technologies, catalog number 18356); a reagent kit for negatively-selecting CTCs from bloods by cross-linking other cells such as erythrocytes and leukocytes other than CTCs and density-gradiently centrifuging the cells (Tumor Cell Enrichment Cocktail; STEMCELL Technologies, catalog number 15167); a reagent kit for concentrating CTCs by using antibody-immobilized magnetic beads and negatively-selecting CTCs using magnets (Tumor Cell Enrichment Cocktail; STEMCELL Technologies, catalog number 14152).

CITATION LIST

Patent Literature

[PATENT LITERATURE 1] US 2002/0172987
[PATENT LITERATURE 2] US 2007/0026469

[PATENT LITERATURE 3] Japanese Unexamined Patent Publication (Kokai) No. 2007-178193
[PATENT LITERATURE 4] Japanese Unexamined Patent Publication (Kokai) No. 2010-181349
[PATENT LITERATURE 5] Japanese Unexamined Patent Publication (Kokai) No. 2006-29921
[PATENT LITERATURE 6] Japanese Translation Publication (Kohyo) No. 2011-515109
[PATENT LITERATURE 7] WO 2011/086990
[PATENT LITERATURE 8] US 2006/0254972
[PATENT LITERATURE 9] Japanese Unexamined Patent Publication (Kokai) No. 2010-14416

Non-Patent Literature

[NON-PATENT LITERATURE 1] The Journal of Clinical Investigation (United States) 2009, vol. 119, p. 3172-3181
[NON-PATENT LITERATURE 2] Breast Cancer Research (Great Britain) 2011, vol. 13, R59
[NON-PATENT LITERATURE 3] Journal of Mammary Gland Biology and Neoplasia (Germany) 2010, vol. 15, p. 117-134
[NON-PATENT LITERATURE 4] Journal of Clinical Oncology (United States) 2011, vol. 29 (suppl 7; abstr41)
[NON-PATENT LITERATURE 5] CytoTrack Poster, 2009, A3.pdf, internet (http://ing.dk/modules/fsArticle/download.php?fileid=550)
[NON-PATENT LITERATURE 6] Cytometry Part A (United States) 2011, vol. 79A, p. 107-117
[NON-PATENT LITERATURE 7] The Journal of Cell Biology (United States) 1984, vol. 99, p. 1424-1433

SUMMARY OF INVENTION

Technical Problem

In the method for detecting and measuring CTCs, it is necessary to detect 1 cell/mL of CTC from $10^9$ cells/mL of other highly concentrated cells such as erythrocytes and leucocytes.

The first problem is related to a detection of CTCs wherein an epithelial-mesenchymal transition is induced, by using EpCAM, as mentioned below.

In the method disclosed in Patent reference 1, a protocol for concentrating CTCs using an anti-EpCAM antibody is employed. However, in Non-Patent reference 2, it is reported that epithelial-mesenchymal transition (EMT) is induced in the CTCs derived from epithelial cancer cells. If the epithelial-mesenchymal transition is induced, it is considered that a single cancer cell which forms a mass of cancer can migrate, and thus the cancer cell can easily metastasize. Further, an expression of EpCAM on cancer cells is reduced by EMT. Therefore, in the method for detecting CTCs by concentrating CTCs using an anti-EpCAM antibody, it is difficult to detect CTCs having a high malignancy and a high metastatic property, wherein EMT is progressively induced.

The second problem is related to an evaluation of the stages of cancer progression according to a ratio of an induction of epithelial-mesenchymal transition, as mentioned below.

It is determined that the more the number (concentration) of CTC increases, the more cancer becomes advanced, on the basis of a correlation between a detected number (concentration) of CTCs in peripheral blood and a patient's prognosis. However, Non-patent reference 2 discloses that a rate of EMT-induced CTC is high in patients with metastatic cancer compared to patients with early-stage cancer. Thus, it is considered that the rate of EMT-induced CTC is related to the patient's prognosis, in addition to the number (concentration) of CTC. That is, it is important to analyze an EMT induction in each of the CTCs. As described in Non-Patent reference 2, in the method for analyzing the EMT induction in each of the CTCs, cytokeratin (CK) and vimentin on CTC are doubly, fluorescently-stained. When it is confirmed from an image of fluorescence microscope that vimentin on CTC is fluorescently-stained in addition to cytokeratin (CK), it is determined that the EMT is induced. According to this report, EMT is induced in 70% or more of the CTCs of patients with early-stage cancer, and EMT is induced in 100% of the CTCs of patients with metastatic cancer. However, as EMT is induced in 70% or more of the CTCs of cancer patients, and thus it is difficult to determine whether or not the cancer cell metastasizes, on the basis of the rate of EMT-induced CTC. This is because the number of detected CTCs is generally about 10 in 7 mL of peripheral blood, and thus about 10 of the number of detected CTCs per se contains an uncertainty of plus or minus 30%, taking into account a statistical error according to Poisson distribution. Therefore, it is meaningless to discuss a variation from 70% (patients with early-stage cancer) to 100% (patients with metastatic cancer) of the rate of the CTCs with EMT, by using the number of detected CTCs with an uncertainty of plus or minus 30%.

That is to say, EMT is induced in 70% of circulating tumor cells of the patients with early-stage cancer, and thus it is very difficult to evaluate a stage of cancer progression or a malignancy of cancer from the rate of EMT induction in circulating tumor cells. Further, it is impossible to adopt the method for evaluating EMT disclosed in Non-patent reference 7, as one for evaluating EMT of the circulating tumor cells wherein the number thereof is low.

The object of the present invention is to provide an evaluation method capable of accurately determining metastasis of cancer, stage of cancer progression, or malignancy of cancer.

Solution to Problem

The present inventors have conducted intensive studies into the evaluation method of circulating tumor cells. As a result, the present inventors, surprisingly, found that the metastasis of cancer, stage of cancer progression, or malignancy of cancer can be accurately diagnosed by measuring an amount of a marker (such as cytokeratin) expressed on a epithelial cell and an amount of a marker (such as vimentin) expressed on a mesenchymal cell, and expressing the same as an EMT index.

The present invention is based on the above findings.

Accordingly, the present invention relates to

[1] a method for detecting the degree of malignancy of each of the circulating tumor cells, characterized by the following steps:

(a) bringing an epithelial cell-binding component which specifically binds to a marker molecule expressed on epithelial cells and is fluorescently-labeled or luminescent enzyme-labeled, and a mesenchymal cell-binding component which specifically binds to a marker molecule expressed on mesenchymal cells and is fluorescently-labeled or luminescent enzyme-labeled, into contact with a sample that possibly contains circulating tumor cells, (b) detecting a fluorescence signal or a luminescence signal of the epithelial cell-binding component and a fluorescence signal or a luminescence signal of the mesenchymal cell-binding component of each of the cells, and (c) determining the degree of epithelial-mesenchymal transition of circulating tumor cells based on the signal amount of the epithelial cell-binding component (E) and the signal amount of the mesenchymal cell-binding component (M),

[2] the method for detecting the degree of malignancy of each of the circulating tumor cells of item [1], further comprising the step of (d) removing erythrocytes and/or leucocytes from the sample, before or after step (a),

[3] the method for detecting the degree of malignancy of each of the circulating tumor cells of item [1] or [2], wherein a leucocyte-binding component, which specifically binds to a marker molecule expressed on leucocytes and is fluorescently-labeled or luminescent enzyme-labeled, is brought into contact with a sample that possibly contains circulating tumor cells in the step (a),

[4] the method for detecting the degree of malignancy of each of the circulating tumor cells of items [1] to [3], wherein the fluorescence signal or the luminescence signal is detected by a flow cytometer or an image analyzer in the detection step (b),

[5] the method for detecting the degree of malignancy of each of the circulating tumor cells of items [1] to [4], wherein the degree of epithelial-mesenchymal transition is represented by a formula selected from a group consisting of formula (1)

$$P=M/(E+M) \qquad (1),$$

formula (2)

$$P=E/(E+M) \qquad (2),$$

formula (3)

$$P=\mathrm{Log}\,[M/(E+M)] \qquad (3), \text{ and}$$

formula (4)

$$P=\mathrm{Log}\,[E/(E+M)] \qquad (4)$$

wherein P is the degree, E is the signal amount of the epithelial cell-binding component, and M is the signal amount of the mesenchymal cell-binding component, in step (c),

[6] the method for detecting the degree of malignancy of each of the circulating tumor cells of items [1] to [5], further comprising the step of (e) setting a reference of state before an onset of epithelial-mesenchymal transition (0) and a reference of state after a termination of epithelial-mesenchymal transition (1) by measuring particles to which a fluorescence substance labeling the epithelial cell-binding component is bound, and particles to which a fluorescence substance labeling the mesenchymal cell-binding component is bound,

[7] the method for detecting the degree of malignancy of each of the circulating tumor cells of item [6], step (e) is carried out together with steps (b) and (c),

[8] the method for detecting the degree of malignancy of each of the circulating tumor cells of items [1] to [7], wherein the epithelial cell-binding component is an antibody or aptamer specifically binding to cytokeratin, EpCAM, or E-cadherin, and the mesenchymal cell-binding component is an antibody or aptamer specifically binding to vimentin, or N-cadherin,

[9] a kit for detecting the degree of malignancy of the circulating tumor cells, comprising (a) an epithelial cell binding antibody which specifically binds to a marker molecule expressed on epithelial cells and is fluorescently-labeled or luminescent enzyme-labeled, and (b) a mesenchymal cell-binding antibody which specifically binds to a marker molecule expressed on mesenchymal cells and is fluorescently-labeled or luminescent enzyme-labeled,

[10] the kit for detecting the degree of malignancy of the circulating tumor cells of item [9], further comprising:

(c) a leucocyte-binding antibody which specifically binds to a marker molecule expressed on leucocytes and is fluorescently-labeled or luminescent enzyme-labeled, and/or (d) particles to which a fluorescence substance or luminescent enzyme labeling the epithelial cell-binding antibody is bound, and (e) particles to which a fluorescence substance or luminescent enzyme labeling the mesenchymal cell-binding antibody is bound,

[11] the kit for detecting the degree of malignancy of the circulating tumor cells of item [9] or [10], wherein the epithelial cell-binding antibody is an antibody specifically binding to cytokeratin, EpCAM, or E-cadherin, and the mesenchymal cell-binding antibody is an antibody specifically binding to vimentin, or N-cadherin,

[12] a use for preparing a kit for detecting the degree of malignancy of the circulating tumor cells, of an epithelial cell binding antibody specifically binding to a marker molecule expressed on epithelial cells, and/or a mesenchymal cell-binding antibody specifically binding to a marker molecule expressed on mesenchymal cells,

[13] the use for preparing a kit for detecting the degree of malignancy of the circulating tumor cells of item [12], wherein the epithelial cell-binding antibody is an antibody specifically binding to cytokeratin, EpCAM, or E-cadherin, and the mesenchymal cell-binding antibody is an antibody specifically binding to vimentin, or N-cadherin

[14] an apparatus for detecting the degree of malignancy of the circulating tumor cells, characterized by comprising:

(a) a means of receiving an amount of fluorescence signal or the luminescence signal of epithelial cell-binding component bound to each of the circulating tumor cells and an amount of fluorescence signal or the luminescence signal of mesenchymal cell-binding component bound to each of circulating tumor cells, and (b) a means of determining the degree of epithelial-mesenchymal transition of each of the circulating tumor cells based on the received amount of signal of the epithelial cell-binding component (E) and the received amount of signal of the mesenchymal cell-binding component (M),

[15] the apparatus for detecting the degree of malignancy of the circulating tumor cells of item [14], wherein the degree of epithelial-mesenchymal transition in the means (b) is represented by a formula selected from a group consisting of formula (1)

$$P=M/(E+M) \qquad (1),$$

formula (2)

$$P=E/(E+M) \qquad (2),$$

formula (3)

$$P=\mathrm{Log}\,[M/(E+M)] \qquad (3), \text{ and}$$

formula (4)

$$P=\mathrm{Log}\,[E/(E+M)] \qquad (4)$$

wherein P is the degree, E is a signal amount of the epithelial cell-binding component, and M is a signal amount of the mesenchymal cell-binding component,

[16] the apparatus for detecting the degree of malignancy of the circulating tumor cells of item [14] or [15], wherein the epithelial cell-binding component is an antibody specifically binding to cytokeratin, EpCAM, or E-cadherin, and the mesenchymal cell-binding component is an antibody specifically binding to vimentin, or N-cadherin,

[17] a method for evaluating cells, characterized in that the amounts of multiple molecules expressed on each of the cells are analyzed in each cell, and the characteristic feature of each cell is quantified and indicated by using the amounts of multiple molecules, in procedures for measuring cells,

[18] the method for evaluating cells of item [17], wherein the amounts of multiple molecules analyzed in each cell are an amount of marker molecules expressed on epithelial cells (E) and an amount of marker molecules expressed on mesenchymal cells (M), the characteristic feature of each cell is a degree of epithelial-mesenchymal transition which is obtained by a formula calculated from E and M,

[19] an apparatus for evaluating cells, characterized in that the apparatus can measure cells, and the amounts of multiple molecules expressed on each of the cells are analyzed in each cell, and the characteristic feature of each cell is quantified and indicated by using the amounts of multiple molecules, in procedures for measuring cells,

[20] the apparatus for evaluating cells of item [19], wherein the amounts of multiple molecules analyzed in each cell are an amount of marker molecules expressed on epithelial cells (E) and an amount of marker molecules expressed on mesenchymal cells (M), the characteristic feature of each cell is a degree of epithelial-mesenchymal transition obtained by a formula calculated from E and M.

Advantageous Effects of Invention

According to the method for detecting the degree of malignancy of each of the circulating tumor cells in the present invention, the metastasis of cancer, stage of cancer progression, or malignancy of cancer can be accurately diagnosed. Specifically, the detecting method of the present invention can be used in an occurrence prediction of metastasis after extirpation of the cancer, or the monitoring of the stages of cancer progression. Further, the present invention can be used in monitoring therapeutic effects of anticancer drugs by measuring CTCs after administration of said anticancer drugs and evaluating the degree of EMT in the CTCs.

DESCRIPTION OF EMBODIMENTS

[1] Method for Detecting the Degree of Malignancy of the Circulating Tumor Cells The method for detecting the degree of malignancy of each of the circulating tumor cells of the present invention comprises the steps of: (a) bringing an epithelial cell-binding component which specifically binds to a marker molecule expressed on epithelial cells and is fluorescently-labeled or luminescent enzyme-labeled, and a mesenchymal cell-binding component which specifically binds to a marker molecule expressed on mesenchymal cells and is fluorescently-labeled or luminescent enzyme-labeled, into contact with a sample that may possibly contain circulating tumor cells, (b) detecting a fluorescence signal or a luminescence signal of the epithelial cell-binding component and a fluorescence signal or a luminescence signal of the mesenchymal cell-binding component of each of the cells, and (c) determining the degree of epithelial-mesenchymal transition of circulating tumor cells based on the signal amount of the epithelial cell-binding component (E) and the signal amount of the mesenchymal cell-binding component (M).

The method for detecting the degree of malignancy of each of the circulating tumor cells of the present invention further comprises the step of (d) removing erythrocytes and/or leucocytes from the sample, before or after step (a).

The detecting method of the present invention can be used as a method for detecting (diagnosing) the metastasis of cancer, a method for detecting (diagnosing) the stage of cancer progression, or a method for monitoring the therapeutic effects in cancer, in particular, for monitoring the therapeutic effects of an anticancer drug.

<<Contact Step (a)>>

In the contact step (a) in the detecting method of the present invention, a sample that may possibly contain circulating tumor cells is brought into contact with an epithelial cell-binding component which specifically binds to a marker molecule expressed on epithelial cells and is fluorescently-labeled or luminescent enzyme-labeled, and a mesenchymal cell-binding component which specifically binds to a marker molecule expressed on mesenchymal cells and is fluorescently-labeled or luminescent enzyme-labeled.

(Epithelial Cell Marker)

The marker expressed on an epithelial cell (hereinafter, referred to as an epithelial cell marker) is not particularly limited as long as it was expressed on the circulating tumor cells, but includes, for example, a surface protein and a sugar chain of an epithelial cell. Specifically, cytokeratin, EpCAM, or E-cadherin can be used as the epithelial cell marker, and in particular, cytokeratin is preferably. As the cytokeratin, at least one cytokeratin selected from a group consisting of CK1, CK4, CK5, CK8, CK10, CK14, CK15, CK16, CK18, and CK19 may be used, but the mixture of two or more thereof is preferable. Further, cytokeratin, EpCAM, and E-cadherin are labeled with the same fluorescence, and the total expression amount thereof can be used as the expression amount of the marker expressed on an epithelial cell. A combination of the above markers is not limited, but contains cytokeratin, preferably.

(Epithelial Cell-Binding Component)

The epithelial cell-binding component which specifically binds to the epithelial cell marker is not limited, so long as it can be bound to the epithelial cell marker, but it includes, for example, antibody, antibody fragment, antigen, DNA, RNA, receptor, ligand for receptor, enzyme, ligand for enzyme, enzyme analog, substrate for the enzyme to be based on enzyme analog, lectin, or sugar chain. Specifically, when the epithelial cell marker is protein, antibody, antibody fragment, ligand for receptor, ligand for enzyme, DNA (such as aptamer), or RNA may be used. Further, when the epithelial cell marker is sugar chain, antibody, antibody fragment, or lectin may be used.

(Marker Expressed on Mesenchymal Cell)

Marker expressed on mesenchymal cell (hereinafter, referred to as a mesenchymal cell marker), is not particularly limited as long as it is expressed on the circulating tumor cells, but includes, for example, a surface protein and a sugar chain of mesenchymal cell. Specifically, vimentin, Twist, and N-cadherin can be used as the mesenchymal cell marker. Further, vimentin, Twist and N-cadherin are labeled by the same fluorescence, and the total expression amount thereof can be used as the expression amount of the marker expressed on the mesenchymal cell. A combination of the above markers is not limited, but contains vimentin, preferably.

(Mesenchymal Cell-Binding Component)

The mesenchymal cell-binding component which specifically binds to the mesenchymal cell marker is not limited so long as it can be bound to the mesenchymal cell marker, but includes, for example, antibody, antibody fragment, antigen, DNA, RNA, receptor, ligand for receptor, enzyme, ligand for enzyme, enzyme analog, substrate for the enzyme to be based on enzyme analog, lectin, or sugar chain. Specifically, when the mesenchymal cell marker is protein, antibody, antibody fragment, ligand for receptor, ligand for enzyme, DNA (such as aptamer), or RNA may be used. Further, when the mesenchymal cell marker is sugar chain, antibody, antibody fragment, or lectin may be used.

(Antibody or Antibody Fragment)

The antibody used as the epithelial cell-binding component or the mesenchymal cell-binding component is not limited, but there may be mentioned, for example, polyclonal antibody, monoclonal antibody, recombinant antibody, or antibody fragment having the antigen-binding site thereof. As the antibody fragment, there may be mentioned, for example, F(ab')$_2$, Fab', Fab, Fv, or the like. The fragment of the antibody may be obtained by conventional methods, for example, by digesting the antibody using a protease (such as pepsin, papain, or the like) and purifying the resulting fragments by standard polypeptide isolation and purification methods.

(Fluorescent Label or Luminescent Enzyme Label)

The epithelial cell-binding component and mesenchymal cell-binding component are preferably fluorescently-labeled, or luminescent enzyme-labeled. A fluorescent substance used for fluorescent labeling is not particularly limited, but there may be mentioned, for example, AMCA, Alexa Flour 350, Murina Blue, Cascade Blue, Cascade Yellow, Pacific Blue, Alexa Flour 405, Alexa Flour 488, Qdot(R)605, FITC, PE/RD1, ECD/PE-TexasRed, PC5/SPRD/PE-Cy5, PC5.5/PE-Cy5.5, PE Alexa Flour 750, PC7/PE-Cy7, TRITC, Cy3, Texas Red, Alexa Flour 647, Alexa Flour 700, Cy5, Cy5.5, APC, APC7/APC-Cy7, APC Alexa Flour 750.

Further, the luminescent enzyme is not particularly limited, but includes luciferase. An origin of the luciferase is not particularly limited, but there may be mentioned a luciferase derived from firefly, or a luciferase derived from bacteria. The luminescent enzyme becomes luminous by reacting with a substrate specific to the luminescent enzyme. Thus, it may be preferably used in the analysis by the image analyzer, as mentioned below. As the substrate of luminescent enzyme, a substrate specific to each luminescent enzyme may be used, and thus, the substrate can be appropriately selected. For example, if the luciferase is used, a luciferin having substrate-specificity to each luciferase may be used.

(Fluorescence or Luminescence Stain of Leucocyte)

The contact step (a) may comprise the procedure of bringing a sample that may possibly contain circulating tumor cells into contact with the leucocyte-binding component which specifically binds to a marker molecule expressed on leucocytes and is fluorescently-labeled or luminescent enzyme-labeled.

By fluorescently-staining the marker expressed on leucocytes, the circulating tumor cells can surely be separated from leucocytes using a flow cytometer or an image analyzer in the following detection step. Thus, an accuracy of detection of circulating tumor cells can be increased.

A leucocyte marker is not particularly limited, so long as it is specifically expressed on leucocytes, but includes, for example, CD45, CD2, CD3, CD4, CD5, CD8, CD10, CD11b, CD14, CD15, CD16, CD19, CD20, CD24, CD25, CD27, CD29, CD33, CD36, CD38, CD41, CD45, CD45RA, CD45RO, CD56, CD66b, CD66e, CD69, or CD124. In particular, CD45 is preferable. This is because most leucocytes have a CD45 marker. Further, the leucocyte-binding component which specifically binds to the leucocytes, is not particularly limited, but includes, for example, antibody, antibody fragment, antigen, DNA, RNA, receptor, ligand for receptor, enzyme, ligand for enzyme, enzyme analog, substrate for the enzyme to be based on enzyme analog, lectin, or sugar chain. However, antibody or antibody fragment is preferable.

An antibody used as the leucocyte-binding component is not limited, but the antibody described in the above item "(Antibody or antibody fragment)" can be used. Further, a fluorescent substance or luminescent enzyme for labeling a leucocyte-binding component is not limited, but the fluorescent substance or luminescent enzyme described in the above item "(Fluorescent label or luminescent enzyme label)" can be used.

(Nuclear Stain)

Further, in the method for detecting the degree of malignancy of circulating tumor cells of the present invention, the nuclear portion of the cells in the sample may be stained. The circulating tumor cells can be surely separated from the cell membrane fragments or the like by nuclear staining.

(Sample)

A sample used in the method for detecting the degree of malignancy of circulating tumor cells of the present invention is not particularly limited, so long as it is a sample obtained from a patient suspected of having cancer. That is, the sample is not limited, so long as the sample may possibly contain circulating tumor cells. Specifically, as the liquid sample that may possibly contain circulating tumor cells, for example, there may be mentioned blood, urine, lymph fluid, tissue fluid, spinal fluid, ascites fluid, or pleural effusion. The peripheral blood is preferable because it is easily collected by drawing blood.

Further, the cancer in the patient in which the sample is collected is an epithelial cancer. As for the epithelial cancer, there may be mentioned bladder cancer, breast cancer, colorectal cancer, rectal cancer, kidney cancer, hepatic cancer, lung cancer, small cell lung cancer, esophageal cancer, gallbladder cancer, ovarian cancer, pancreatic cancer, stomach cancer, cervical cancer, thyroid cancer, prostate cancer, squamous cancer, skin cancer, duodenal cancer, vaginal cancer, or brain cancer.

The term "circulating tumor cells" as used herein means extremely-low concentrated cancer cells detected in the blood of cancer patients. It is sometimes referred to as "circulating tumor cells in blood" or "circulating tumor cells in peripheral blood".

The circulating tumor cells detected in the present invention are not particularly limited. However, the circulating tumor cells are derived from epithelial cancer, preferably. A circulating tumor cell capable of inducing epithelial-mesenchymal transition (EMT) is preferable. There is a report that a half-life of the circulating tumor cells (cancer cells) is 1 to 2.4 hours. Many of the circulating tumor cells are killed by apoptosis. Thus, about several to several dozen of the circulating tumor cells merely exist in $10^9$/mL of the blood cells.

<<Detection Step (b)>>

In the detection step (b), a fluorescence signal or a luminescence signal of epithelial cell-binding component or mesenchymal cell-binding component bound to circulating tumor cells is detected.

The fluorescence or luminescence signal bound to the epithelial cell marker or mesenchymal cell marker is measured on each of the circulating tumor cells. A cell having a certain threshold amount or more of fluorescence or luminescence signal of the epithelial cell marker is detected as the circulating tumor cells.

In order to detect the fluorescence or luminescence signal of circulating tumor cells, an apparatus capable of identifying a single cell is required. For example, a flow cytometer, or an image analyzer can be used.

(Measurement Using Flow Cytometer)

Specifically, a flow cytometer using a disposable micro flow path chip is preferable, in view of the prevention of cross-contamination between samples. Further, a fluorescence signal of each of the low-concentrated CTCs can be detected with high-speed in the flow cytometer. Therefore, it is preferable to measure CTCs by using the above flow cytometer disclosed in Patent references 4 and 9, wherein the measurement without a cross-contamination of samples can be achieved through the disposable micro flow path chip. In the flow cytometer, the fluorescently-stained cells are measured. Further, the measured data is the fluorescent signal intensity of each of the cells, and therefore the signal intensity can be used to quantify a degree of epithelial-mesenchymal transition of each of the cells. This feature is different from the following measurement using the image analyzer.

(Measurement Using Image Analyzer)

In the image analyzer, the fluorescently-stained cells or self-luminously-stained cells are measured. That is, a distribution of fluorescent intensity or luminescence intensity of cells is measured. Therefore, the measured data of the image analyzer is different from that of a flow cytometer. In particular, it is an image of light intensity distribution showing several cells in a defined area. Thus, in order to quantify the signal of each of the cells, a function for tracing an outline of the cell by image recognition is required. Specifically, an integral quantity of the fluorescent intensity distribution of an epithelial cell-binding component within the outline of the cell, and an integral quantity of fluorescent intensity distribution of the mesenchymal cell-binding component within the outline of the cell are calculated. Then, when the degree of epithelial-mesenchymal transition is quantified in the next step, the above integral quantities are essentially used.

<<Degree Determination Step (c)>>

In the degree determination step (c), the degree of epithelial-mesenchymal transition is quantified by the signal amount of the epithelial cell-binding component (E) and the signal amount of the mesenchymal cell-binding component (M).

The signal amount of the epithelial cell-binding component (E) means the expression amount of the epithelial cell marker on a circulating tumor cell, and the signal amount of the mesenchymal cell-binding component (M) means the expression amount of the mesenchymal cell marker on a circulating tumor cell. Thus, the degree of epithelial-mesenchymal transition is quantified using the expression amount of the epithelial cell marker and the expression amount of the mesenchymal cell marker.

(Procedure for Quantifying Degree of EMT)

The index of degree of EMT is not limited, as long as it is calculated using the signal amount (E) of the epithelial cell-binding component and the signal amount (M) of the mesenchymal cell-binding component and a ratio between the signal amount (M) and the signal amount (E) changes. In particular, an index wherein the more the signal amount (M) with respect to the signal amount (E) increases, the more the degree of EMT increases, is referred to as the "EMT index (P)" herein.

Therefore, as a preferable formula of the EMT index (P), for example, there may be mentioned the following:

Formula (1)

$$P=M/(E+M) \qquad (1).$$

The above EMT index (P) is advantageous from the viewpoint of defining the scope of the upper limit and lower limit from 0 to 1. On the other hand, for example, if an EMT index (P) is "M/E", an obtained value may vary from zero to infinity. However, the closer the value of E is to zero, the more the EMT index (P) increases. That is, when the value of E is close to a detection limit that is not accurate, the EMT index (P) increases. Thus, the EMT index (P) of "M/E" is unfavorable for an index of diagnosis.

While, as a formula of the EMT index (P) showing the degree of EMA, the following formula may be used.

Formula (2)

$$P=E/(E+M) \qquad (2)$$

In this case, a value of 1 means that the EMT is not induced. The above EMT index (P) is advantageous from the viewpoint of defining the scope of the upper limit and lower limit. In addition, the above EMT index (P) may be expressed as a logarithm thereof.

According to the after-mentioned Examples, the EMT index (P) will be concretely explained.

$$P=[(\text{Vimentin expression amount in CTC})/((\text{CK expression amount in CTC})+(\text{Vimentin expression amount in CTC}))]$$

When the EMT is not induced, the above P is zero. When the Vimentin expression amount increases, the above P is close to 1. Thus, the lower limit of zero and the upper limit of 1 are defined as values showing the degree of the EMT. Therefore, the above P can be suitably used as an index for a common diagnostic standard even in different apparatuses.

A concrete procedure for measuring the EMT index is as follows. CK on CTC is stained by FITC labeled anti CK antibody. Then a fluorescence of FITC is measured at a wavelength range of 510 nm to 550 nm, and the resulting signal intensity is referred to as FL1. Further, Vimentin on CTC is stained by a PE labeled anti Vimentin antibody. Then a fluorescence of said PE is measured at a wavelength range of 550 nm to 600 nm, and the resulting signal intensity is referred to as FL2. The EMT index (P) can be shown as a formula of [A(FL2/(FL1+FL2))+B] wherein A and B are apparatus constants. The A is the apparatus constant based on variability between apparatuses of detection sensitivity of fluorescence of FL1 and FL2, and the B is the apparatus constant defined by the zero level of the fluorescence signal. The constants are defined in such a way that P is 0 in the case of the Vimentin expression amount of 0, and P is 1 in the case of the CK expression amount of 0 and only the Vimentin expression. In connection to this, the type of fluorescence substance is not limited to the above types.

The apparatus constants of A and B can be determined as follows.

In order to obtain a standard linear of fluorescence signals of a condition "100% CK (FITC)" wherein cytokeratin only expresses and vimentin does not express, it is necessary to measure cells singly-stained by FITC. However, the preparation of such cells in addition to a sample to be tested on a patient requires time. Thus, a standard linear may be obtained by measuring particles wherein FITC is bound thereto using a flow cytometer. Similarly, a standard linear of fluorescence signals of a condition "100% Vimentin (PE)" wherein vimentin only expresses and cytokeratin does not express, may be obtained by measuring particles wherein PE is bound thereto using the flow cytometer. When two kinds of such standard particles having a single fluorescence spectrum and the CTCs of the sample are simultaneously measured, a determination of reference as to the upper and lower limits of the EMT index, and the analysis of the EMT index of CTCs of the sample can be conducted simultaneously, and whereby the variability between apparatuses in the analysis of the EMT index can be surely corrected. The correction is important when a common threshold value is applied to the results obtained from various apparatuses.

Figure 3:
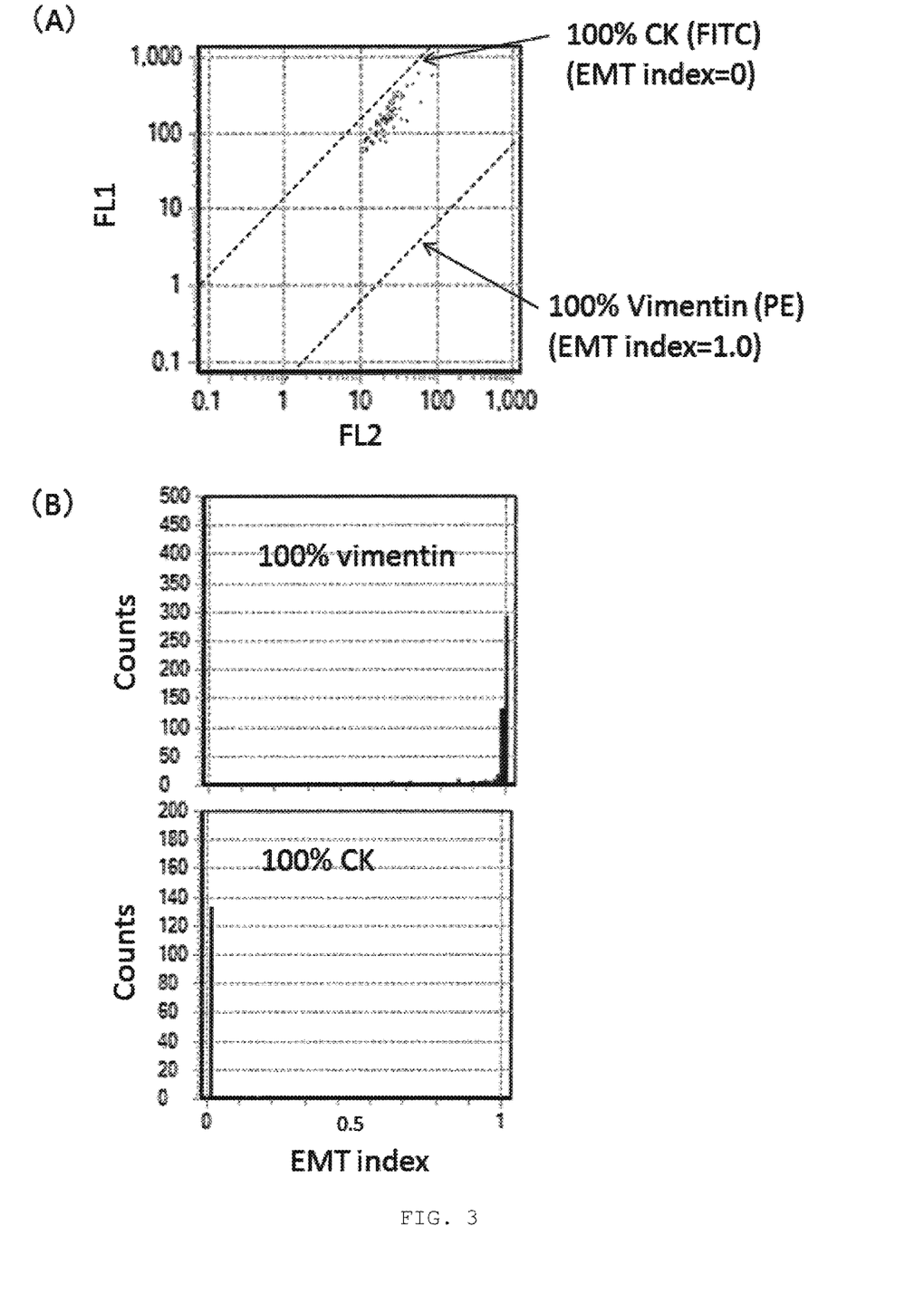
FIG. 3 is a histogram showing the relationship between EMT index and intensity of fluorescence signal (A), and histograms showing EMT indexes of 0% of the degree of EMT and 100% of the degree of EMT (B).

The line of "100% CK (FITC)" drawn in a scatter plot of FIG. 3(A) is defined by a ratio between FL1 of the fluorescence spectrum of FITC and FL2, and data of particles or cells only having fluorescence of FITC are distributed thereon. Similarly, data of particles or cells only having fluorescence of PE are distributed on the line of "100% Vimentin (PE)". The apparatus constants A and B are defined in such a way that the EMT indexes of two kinds of data, i.e. "100% CK (FITC)" and "100% Vimentin (PE)" are 0 and 1 respectively.

(Epithelial-Mesenchymal Transition)

When the epithelial-mesenchymal transition is induced, a cell-to-cell adhesiveness is decreased by a transition from epithelial cell to mesenchymal cell. If the EMT is induced in cancer cells, the cancer cells are removed from cancer tissue. Thus, it is considered that the induced EMT leads to an increase of metastatic potential of cancer cells, and therefore the malignancy of cancer cells progresses. In connection to this, if the signal amount (E) of the epithelial cell-binding component is major, the stage of cancer progression is low. If the signal amount (M) of the mesenchymal cell-binding component is major, the stage of cancer progression is high. The signal amount (E) of the epithelial cell-binding component means the expression amount of the epithelial cell marker, and the signal amount (M) of the mesenchymal cell-binding component means the expression amount of the mesenchymal cell marker.

Non-Patent reference 2 discloses that EMT is induced in 70% or more of the CTCs of patients with early-stage cancer, and EMT is induced in 100% of the CTCs of patients with metastatic cancer. However, Non-Patent reference 2 does not disclose that a stage of cancer progression in a single cell varies by the expression amount of an epithelial cell marker such as cytokeratin, and the expression amount of a mesenchymal cell marker such as vimentin.

In the method for detecting the degree of malignancy of the circulating tumor cells, the malignancy of circulating tumor cells, the prediction of metastasis of cancer, or the stage of cancer progression can be determined by using the EMT index, i.e. the ratio between the signal amount (E) of the epithelial cell-binding component and the signal amount (M) of the mesenchymal cell-binding component. Further, the occurrence prediction of metastasis after the extirpation of cancer, monitoring the stages of cancer progression, or the monitoring therapeutic effects of anticancer drugs can be performed by using the EMT index.

<<Removal step (d)>>

The method for detecting the degree of malignancy of the circulating tumor cells further comprises the step of (d) removing erythrocytes and/or leucocytes from the sample. The removal step (d) is not an essential step in the detection method of the present invention. However, as about several to several dozen of the circulating tumor cells merely exist in $10^9$/mL of blood cells, it is preferable to remove erythrocytes and/or leucocytes before or after the contact step (a). In particular, the removal step (d) is preferably carried out before the contact step (a). The epithelial cell marker and the mesenchymal cell marker on the CTCs are effectively stained by conducting the removal step (d) before the contact step (a).

The protocol for removing erythrocytes is not particularly limited. However, ammonium chloride solution for removing erythrocytes, or commercially available buffers for removing erythrocytes can be used.

Further, the protocol for removing leucocytes is not particularly limited, but there may be mentioned the negative selection of leucocytes using antibody-immobilized magnetic beads against a surface marker of leucocytes and a magnet. This protocol is preferable because it is an EpCAM-independent, enrichment method.

<<Reference Setting Step (e)>>

The method for detecting the degree of malignancy of the circulating tumor cells of the present invention further comprises the step of (e) setting a reference of state before an onset of epithelial-mesenchymal transition (0) and a reference of state after a termination of epithelial-mesenchymal transition (1) by measuring particles to which a fluorescence substance labeling the epithelial cell-binding component is bound, and particles to which a fluorescence substance labeling the mesenchymal cell-binding component is bound. The "particles to which a fluorescence substance labeling the epithelial cell-binding component is bound" corresponds to the particles wherein FITC is bound thereto, and the "particles to which a fluorescence substance labeling the mesenchymal cell-binding component is bound" corresponds to the particles wherein PE is bound thereto. However, the fluorescence substance is not limited to FITC or PE, but, for example, the fluorescence substances described in the item "(Fluorescent label or luminescent enzyme label)" can be used. Further, a particle is not particularly limited as long as it can be used in a flow cytometer or image analyzer, but includes cells or beads having a uniform size.

In the method for detecting the degree of malignancy of the circulating tumor cells of the present invention, the reference setting step (e) may be carried out independently. Further, it may be carried out together with detection of particles in the detection step (b). Furthermore, it may be carried out simultaneously in the degree determination step (c). However, if it is carried out in step (b) or (c), beads having uniform and smaller size than cells are preferably used, in order to distinguish beads from the circulating tumor cells.

(Determination of Threshold Value of Cancer Malignancy)

FIG. 3 shows a method for determining threshold value, in order to use the analysis results of malignancy of CTCs in addition to the conventional measured number of CTCs for diagnosis.

The detection and measurement of CTCs are carried out by the contact step (a) and the detection step (b). Further, the EMT index is calculated by the degree determination step (c), and thereby the degree of epithelial-mesenchymal transition of each of the circulating tumor cells is determined. Then, "when the number of circulating tumor cells having a certain EMT index or more is more than the predetermined number (threshold value)" or "when an average of EMT index is more than the predetermined value (threshold value)", it can be determined that, for example, "the patient has metastasis of cancer at the high frequency". Further, when the number of CTCs or EMT index are not more than the predetermined value (threshold value), it can be determined that, for example, the patient has a low possibility of metastasis of cancer. Similarly, when the number of CTCs or EMT index are more than the predetermined threshold value (cutoff value), it can be determined that "malignancy of cancer is high", "stage of cancer is progressed", "effects of anticancer drug is low", or the like. When the number of CTCs or EMT index are not more than the predetermined value (threshold value: cutoff value) to the contrary, it can be determined that "malignancy of cancer is low", "stage of cancer is not progressed", "effects of anticancer drug is high", or the like. The predetermined value (threshold value: cutoff value) can be appropriately determined according to each situation.

The predetermined value (threshold value: cutoff value) can be determined without limitation, as long as the metastasis of cancer, the malignancy of cancer, the stage of cancer progression, or the like is diagnosed. That is to say, the various predetermined value (threshold value: cutoff value) can be used according to each situation. However, the predetermined value (threshold value: cutoff value) is preferably determined by a controlled clinical trial.

[2] Kit for Detecting the Degree of Malignancy of the Circulating Tumor Cells

The kit for detecting the degree of malignancy of the circulating tumor cells of the present invention comprises (a) an epithelial cell-binding antibody which specifically binds to a marker molecule expressed on epithelial cells and is fluorescently-labeled or luminescent enzyme-labeled, and (b) a mesenchymal cell-binding antibody which specifically binds to a marker molecule expressed on mesenchymal cells and is fluorescently-labeled or luminescent enzyme-labeled. Further, the kit for detecting the degree of malignancy of the circulating tumor cells of the present invention further comprises (c) a leucocyte-binding antibody which specifically binds to a marker molecule expressed on leucocytes and is fluorescently-labeled or luminescent enzyme-labeled and/or (d) particles to which a fluorescence substance or luminescent enzyme labeling the epithelial cell-binding antibody is bound, and (e) particles to which a fluorescence substance or luminescent enzyme labeling the mesenchymal cell-binding antibody is bound.

The detection kit of the present invention can be used for a method of detecting the degree of malignancy of each of the circulating tumor cells. Therefore, the detection kit of the present invention can also be used for the method for detecting (diagnosing) the metastasis of cancer, the method for detecting (diagnosing) the stage of cancer progression, or the method for monitoring the therapeutic effects in cancer, in particular, for monitoring the therapeutic effects of an anticancer drug. That is, the detection kit of the present invention may be used as a kit for the above methods.

<<Epithelial Cell-Binding Antibody (a)>>

The epithelial cell-binding antibody (a) can specifically bind to the epithelial cell marker described in the detection method of the present invention. As the epithelial cell marker, there may be mentioned one stated in the above item "(Epithelial cell marker)", more preferably cytokeratin, EpCAM, or E-cadherin.

The antibody is not particularly limited, as long as it can bind to the epithelial cell marker, but includes polyclonal antibody, monoclonal antibody, recombinant antibody, or antibody fragment having the antigen-binding site thereof. As for the antibody fragment, there may be mentioned, for example, $F(ab')_2$, Fab', Fab, Fv, or the like. The fragment of the antibody may be obtained by conventional methods, for example, by digesting the antibody using a protease (such as pepsin, papain, or the like) and purifying the resulting fragments by standard polypeptide isolation and purification methods.

<<Mesenchymal Cell-Binding Antibody (b)>>

The mesenchymal cell-binding antibody (b) can specifically bind to the mesenchymal cell marker described in the detection method of the present invention. As the mesenchymal cell marker, there may be mentioned one stated in the above item "(Mesenchymal cell marker)", more preferably vimentin, or N-cadherin.

The antibody is not particularly limited, as long as it can bind to the mesenchymal cell marker, but includes polyclonal antibody, monoclonal antibody, recombinant antibody, or antibody fragment having the antigen-binding site thereof. As for the antibody fragment, there may be mentioned, for example, $F(ab')_2$, Fab', Fab, Fv, or the like. The fragment of the antibody may be obtained by conventional methods, for example, by digesting the antibody using a protease (such as pepsin, papain, or the like) and purifying the resulting fragments by standard polypeptide isolation and purification methods.

<<Leucocyte-Binding Antibody (c)>>

The leucocyte-binding antibody (c) can specifically bind to the leucocyte marker described in the detection method of the present invention. As the leucocyte marker, there may be mentioned markers stated in the above item "(Fluorescence or luminescence stain of leucocyte)", more preferably CD45.

The antibody is not particularly limited, as long as it can bind to the leucocytes marker, but includes polyclonal antibody, monoclonal antibody, recombinant antibody, or antibody fragment having the antigen-binding site thereof. As for the antibody fragment, there may be mentioned, for example, $F(ab')_2$, Fab', Fab, Fv, or the like. The fragment of the antibody may be obtained by conventional methods, for example, by digesting the antibody using a protease (such as pepsin, papain, or the like) and purifying the resulting fragments by standard polypeptide isolation and purification methods.

(Fluorescent Label or Luminescent Enzyme Label)

The epithelial cell-binding antibody (a), mesenchymal cell-binding antibody (b), and leucocyte-binding antibody (c) are fluorescently-labeled or luminescent enzyme-labeled. Further, as the fluorescent substance or luminescent enzyme, one generally known in this field can be used without limitation. For example, the fluorescent substance or luminescent enzyme described in the above item "(Fluorescent label or luminescent enzyme label)" can be used.

(Particles to which Fluorescence Substance or Luminescent Enzyme Labeling the Epithelial Cell-Binding Antibody is Bound)

The kit of the present invention may comprise particles to which a fluorescence substance or luminescent enzyme labeling the epithelial cell-binding antibody (a) is bound. The particles are used to determine a standard linear (100% CK (FITC)) of the circulating tumor cells which merely express an epithelial cell marker as described in FIG. 3. Therefore, when the epithelial cell-binding antibody (a) is labeled by FITC, the particles also are labeled by FITC.

(Particles to which Fluorescence Substance or Luminescent Enzyme Labeling the Mesenchymal Cell-Binding Antibody is Bound)

The kit of the present invention may comprise particles to which a fluorescence substance or luminescent enzyme labeling the mesenchymal cell-binding antibody is bound. The particles are used to determine a standard linear (100% vimentin (PE)) of the circulating tumor cells which merely express a mesenchymal cell marker as described in FIG. 3. Therefore, when the mesenchymal cell-binding antibody (a) is labeled by PE, the particles are also labeled by PE.

The kit of the present invention may contain a manual that describes the use of the particles to which the fluorescence substance or luminescent enzyme is bound, and/or the calculation of the EMT index.

The particles, to which the fluorescence substance or luminescent enzyme is bound, are not particularly limited. As for the particles, for example, cells may be used, or polystyrene beads containing a single fluorescence substance may be used. The diameter of the particle is not particularly limited, but preferably a bit smaller than the diameter of the cell. The range of diameter is preferably 3 to 6 μm, and a uniform diameter thereof is preferable.

(Use of Antibody or Particle for Preparing the Kit for Detecting the Degree of Malignancy of the Circulating Tumor Cells)

The epithelial cell-binding antibody (a), which specifically binds to a marker molecule expressed on epithelial cells, can be used to prepare the kit for detecting the degree of malignancy of the circulating tumor cells. Further, the mesenchymal cell-binding antibody (b), which specifically binds to a marker molecule expressed on mesenchymal cells, can be used to prepare the kit for detecting the degree of malignancy of the circulating tumor cells. The above-mentioned epithelial cell-binding antibody (a) and the above-mentioned mesenchymal cell-binding antibody (b) can be used for preparation. Further, the leucocyte-binding antibody (c) can be used to prepare the kit for detecting the degree of malignancy of the circulating tumor cells.

The particles to which a fluorescence substance or luminescent enzyme labeling the epithelial cell-binding antibody is bound, and the particles to which a fluorescence substance or luminescent enzyme labeling the mesenchymal cell-binding antibody is bound, can also be used to prepare the kit for detecting the degree of malignancy of the circulating tumor cells.

[3] Apparatus for Detecting the Degree of Malignancy of the Circulating Tumor Cells The apparatus for detecting the degree of malignancy of the circulating tumor cells of the present invention comprises (a) a means of receiving an amount of fluorescence signal or the luminescence signal of the epithelial cell-binding component bound to each of the circulating tumor cells and an amount of fluorescence signal or the luminescence signal of the mesenchymal cell-binding component bound to each of circulating tumor cells, and (b) a means of determining the degree of epithelial-mesenchymal transition of each of the circulating tumor cells based on the received amount of signal of the epithelial cell-binding component (E) and the received amount of signal of the mesenchymal cell-binding component (M).

(Means of Receiving)

The detecting apparatus of the present invention can be used for the method for detecting the degree of malignancy of each of the circulating tumor cells, and has a means for receiving fluorescence signal amounts or the luminescence signal amounts of the epithelial cell-binding component, and fluorescence signal amounts or the luminescence signal amounts of the mesenchymal cell-binding component. Specifically, as for the means, there may be mentioned a fluorescence detector or an emission detector.

(Means of Determining the Degree)

The means of determining the degree comprises the means capable of calculating the EMT index from the received signal amount of the epithelial cell-binding component (E) and the received signal amount of the mesenchymal cell-binding component (M). For example, the EMT index can be calculated by using a programmed computer, after measuring E and M.

A definitional equation of the EMT index is not limited so long as it means a ratio between the signal amount of the epithelial cell-binding component (E) and the signal amount of the mesenchymal cell-binding component (M), but includes formulas "M/(E+M)", "E/(E+M)", "Log [M/(E+M)]", and "Log [E/(E+M)]".

For example, the definitional identity can be expressed by formula (1)

$$P = M/(E+M) \tag{1},$$

formula (2)

$$P = E/(E+M) \tag{2},$$

formula (3)

$$P = \mathrm{Log}\,[M/(E+M)] \tag{3, or}$$

formula (4)

$$P = \mathrm{Log}\,[E/(E+M)] \tag{4}$$

wherein P is degree, E is an amount of the signal of the epithelial cell-binding component, and M is an amount of the signal of the mesenchymal cell-binding component.

In the detecting apparatus of the present invention, the means of receiving and the means of determining the degree can be conducted according to a computer program.

EXAMPLES

The present invention will now be further illustrated by, but is by no means limited to, the following Examples.

Example 1

In this Example, in order to establish the detection method of the present invention, A549 cell line derived from lung cancer was mixed with the peripheral blood of the volunteer, as a substitute for CTC. Then, cytokeratin and vimentin were detected and the EMT index was calculated.

Specifically, 45 mL of lysing buffer was added to 4 mL of peripheral blood in which A549 cells (100 cells) were mixed, and the whole was mixed and allowed to stand on ice so as to lyse erythrocytes. 0.1 mL of solution wherein ImmunoTOKUI (On-chip Biotechnologies Co., Ltd) was diluted by a factor of 20 with PBS buffer containing 0.5% BSA and 2 mM EDTA (hereinafter referred to as T-buffer) was added thereto. The mixture was centrifuged, and the supernatant was aspirated so as to obtain a cell pellet. The resulting cell pellet was resuspended in 200 μL of T-buffer, and 100 μL of Fc Blocking Reagent was added thereto. The whole was incubated at 4° C. for 15 minutes. After the incubation, 200 μL of T-buffer was added to the whole so as to obtain a cell suspension.

The beads immobilized with a CD45 antibody for removing leucocytes were prepared as follows. 400 μL of magnetic beads immobilized with a CD45 antibody (Dynabeads, Life technologies) was poured into an Eppendorf tube. 400 μL of T-buffer was added to the beads and the whole was gently mixed by moving the tube up and down. Then a magnet was brought close to the tube, and the tube was allowed to stand for about 1 minute so that the beads were completely trapped on the wall of the tube. The supernatant was gently removed, and 400 μL of T-buffer was added to the beads. Then the mixture was stirred by a tapping to obtain a Dynabeads mixture.

400 μL of the Dynabeads mixture was added to 500 μL of the cell suspension, and the whole was rotated at 4° C. at 20 rpm for 30 minutes, so that the beads were reacted with cells. The tube was brought close to the magnet, and the tube was allowed to stand for about 10 seconds so that the beads were completely trapped on the wall of the tube. The supernatant was gently removed, and 500 μL of T-buffer was added to the beads and the mixture was stirred. The mixture was centrifuged at 600 g for 5 minutes and a supernatant was removed. 10 mL of 1×BD Lyse/Fix buffer diluted with deionized water was added thereto. The mixture was gently stirred by moving the tube up and down, and was allowed to stand at room temperature for 20 minutes. After the fixation of the cells, the mixture was centrifuged at 600 g for 5 minutes, and the cells were washed by 2 mL of T-buffer again.

The cells were centrifuged at 600 g, for 5 minutes. Then the cells were resuspended with 30 uL of antibody reaction liquid containing 4 μL of antibodies i.e. Alexa700-labelled anti-CD45 antibody, PE-labelled anti-vimentin antibody, FITC-labelled anti-cytokeratin antibody, and 26 μL of T-buffer, and were reacted with antibodies at 4° C. 1 mL of T-buffer was added thereto, and then the cells were centrifuged at 600 g for 5 minutes. The cells were resuspended in 200 μL of T-buffer so as to obtain a sample stained with Alexa700-labelled anti-CD45 antibody, PE-labelled anti-vimentin antibody, and FITC-labelled anti-cytokeratin antibody.

Next, a measurement without cross contamination between samples by the flow cytometry was conducted. In particular, the measurement was carried out using a flow cytometer (FISHMAN-R™, On-chip Biotechnologies Co., Ltd) wherein the disposable micro flow path chip made of acrylic resin is used as the flow cell. In this apparatus, four fluorescences can be detected, and the detected signals are shown as FL1, FL2, FL3, and FL4, respectively. The wavelength regions of FL1, FL2, FL3, and FL4 are 510 nm to 550 nm, 565 nm to 605 nm, 656 nm to 696 nm, and 700 nm to 850 nm, respectively.

The resulting sample was applied to the flow cytometer, and FITC-labelled anti-cytokeratin antibody, PE-labelled anti-vimentin antibody, nuclear staining agent i.e. 7-AAD, and Alexa700-labelled anti-CD45 antibody were detected by FL1, FL2, FL3, and FL4, respectively. The EMT index was calculated according to the following procedures.

Figure 1:
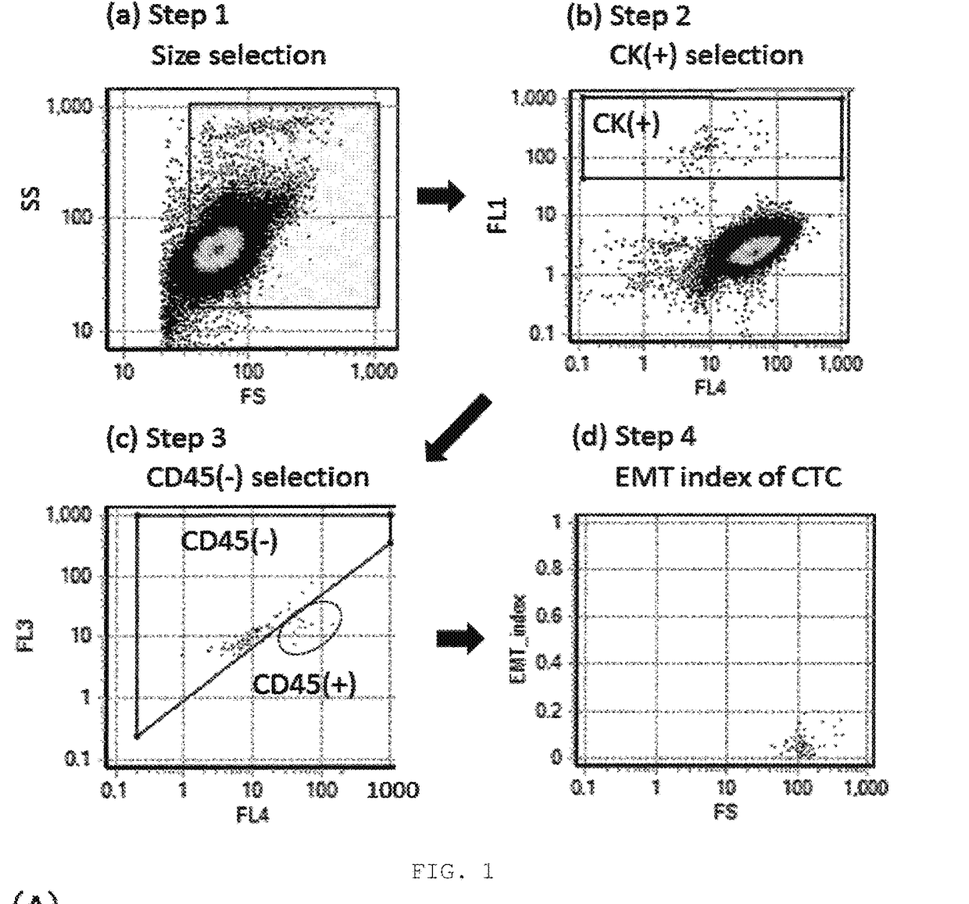
FIG. 1 is a view showing an analysis process for obtaining an EMT index of the CTC from measured data. The scatter plot between a forward scattered signal (FS) and a sideward scattering signal (SS) (a); the scatter plot between FL1 corresponding to FITC and FL4 corresponding to ALEXA700 (b); the scatter plot between the spectrum of nuclear staining by 7-AAD (FL3) and spectrum of ALEXA700 (FL4) (c); and the graph showing EMT indexes calculated using FL1 and FL2 (d), are shown.
Figure 2:
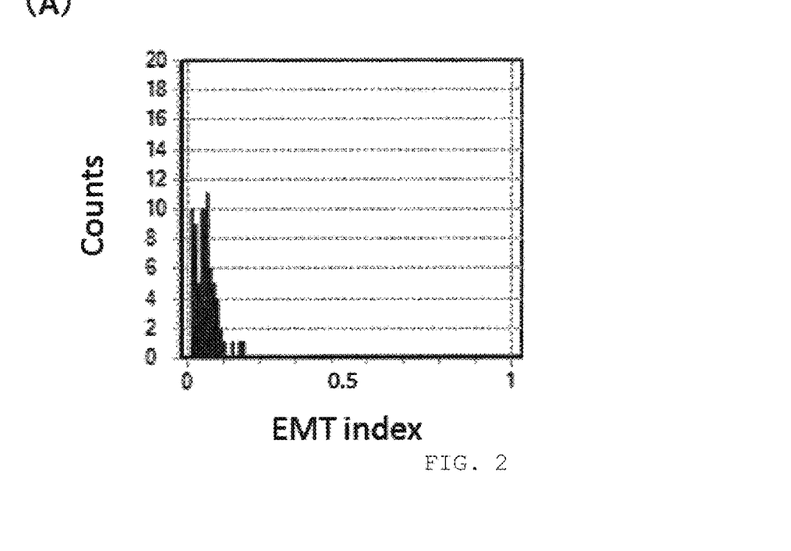
FIG. 2 is a histogram showing the evaluated EMT index of the A549 cell line mixed into peripheral blood.

In FIG. 1(a), the scatter plot between the forward scattered signal (FS) and the sideward scattering signal (SS) is shown. One dot in the scatter plot corresponds to one cell. Many of the cells are leucocytes which were supposed to be removed by the magnetic beads. It was found that an enormous number of leucocytes other than CTCs are contained therein. Firstly, small cellular fragments were removed from the scatter plot. In FIG. 1(b), the scatter plot FL1 corresponding to FITC and FL4 corresponding to ALEXA700 is shown. The CK positive cells labelled with FITC were selected from the scatter plot. In FIG. 1(c), the scatter plot showing FL3 corresponding to the spectrum of 7-AAD and FL4 corresponding to the spectrum of ALEXA700 is described. Leucocytes were completely removed by selecting the CD45 negative cells from the scatter plot. FIG. 1(d) is a graph showing the EMT index of CK-positive CTC cells not containing leucocytes, which is calculated using FL1 and FL2. In the scatter plot, the EMT index on a longitudinal axis and the FS on an abscissa axis are plotted. It was found that the EMT indexes of A549 cells were distributed on about 10%. The histogram of the EMT index values of CTCs is shown in FIG. 2.

Example 2

In this example, a method for determining the apparatus constants A and B of the flow cytometer in the formula i.e. EMT index=[A(FL2/(FL1+FL2))+B] used in Example 1 is explained.

In order to obtain a standard linear of fluorescence signals of a "100% CK (FITC)" condition wherein cytokeratin only expresses and vimentin does not express, particles bound with FITC were measured by the flow cytometer. Further, in order to obtain a standard linear of fluorescence signals of a "100% Vimentin (PE)" condition wherein vimentin only expresses and cytokeratin does not express, particles bound with PE were measured by the flow cytometer.

In particular, the apparatus constants A and B are calculated as follows.

In order to obtain a standard linear of fluorescence signals of a "100% CK (FITC)" condition wherein cytokeratin only expresses and vimentin does not express, the FITC-bound particles having a diameter of 3 μm were measured by the flow cytometer so as to obtain a standard linear. Further, in order to obtain a standard linear of fluorescence signals of a "100% Vimentin (PE)" condition wherein vimentin only expresses and cytokeratin does not express, PE-bound particles having a diameter of 3 μm were measured by the flow cytometer. The apparatus constants A and B are defined in such a way that the values of EMT indexes of the above two types of particles are 0 and 1, respectively. This will be illustrated in the use of FIG. 2.

In FIG. 2(A), the relationship between an EMT value and a fluorescence signal value is shown. The dashed line "100% CK (FITC)" described in FIG. 2 is a standard linear of 100% FITC (cytokeratin), which is obtained by the measurement values of FITC-bound particles. The dashed line "100%

Vimentin (PE)" described in FIG. 2 is a standard linear of 100% PE (vimentin), which is obtained by the measurement values of PE-bound particles. If the cytokeratin or vimentin is singly expressed on a cell, the dot of the cell is on the standard linear of either of them.

The cytokeratin is labelled with FITC, and thus, the CTC data, wherein the cytokeratin is only expressed thereon (100%) and the EMT is not induced, is distributed on the standard linear of "100% CK (FITC)" corresponding to the FITC fluorescence spectrum. When a CTC is on the above standard linear of "100% CK (FITC)", an EMT index value thereof is zero (0). On the other hand, when the vimentin is only expressed thereon (100%), the CTC data is distributed on the standard linear of "100% Vimentin (PE)" corresponding to the PE fluorescence spectrum. When a CTC is on the standard linear of "100% Vimentin (PE)", an EMT index value thereof is 1.

FIG. 3(B) is a set of histograms showing the data of particles bound with PE and the data of particles bound with FITC. The apparatus constants A and B are initially set in such a way that the modes thereof are 1 and 0 (zero), respectively. Therefore, the distributions of EMT indexes between various apparatuses can be compared. Generally, raw data of fluorescence signal intensity in flow cytometry may not be compared between various apparatuses with differences or the like. However, an index for medical diagnosis which can be used for comparison between various apparatuses is required. The above EMT index satisfies this request.

Example 3

In this Example, recovery rates in the detection method of the present invention were examined by using A549 cells or cancer cells other than A549 cells.

The procedures described in Example 1 were repeated using A549 cells. Further, the procedures described in Example 1 were repeated except that KATO-III cells, PC-9 cells, or PC-14 cells were used instead of A549 cells. Then, EMT indexes thereof were calculated, and further detection rates of these cells were calculated simultaneously.

Figure 4:
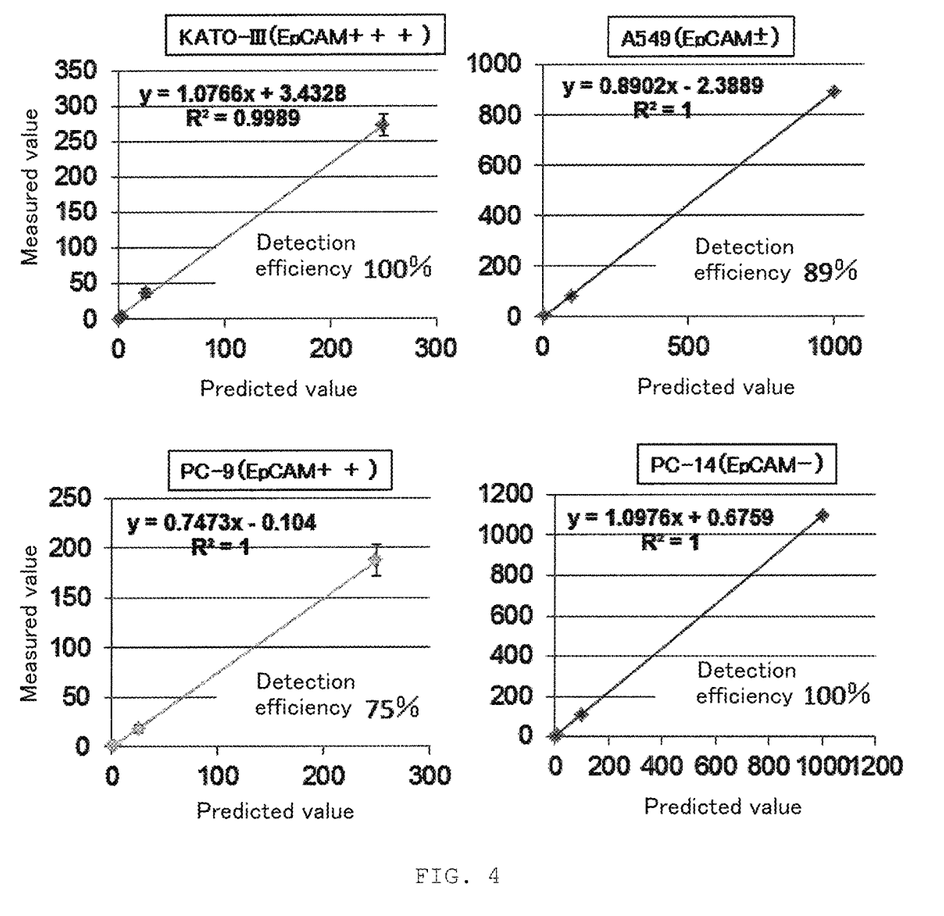
FIG. 4 is a set of graphs showing the evaluation results of detection efficiencies of various cell lines mixed into peripheral blood of a normal human. The graphs show that a cell line of 0% of EpCAM expression can be detected, and the CTC wherein EMT is progressively induced can also be detected.
Figure 5:
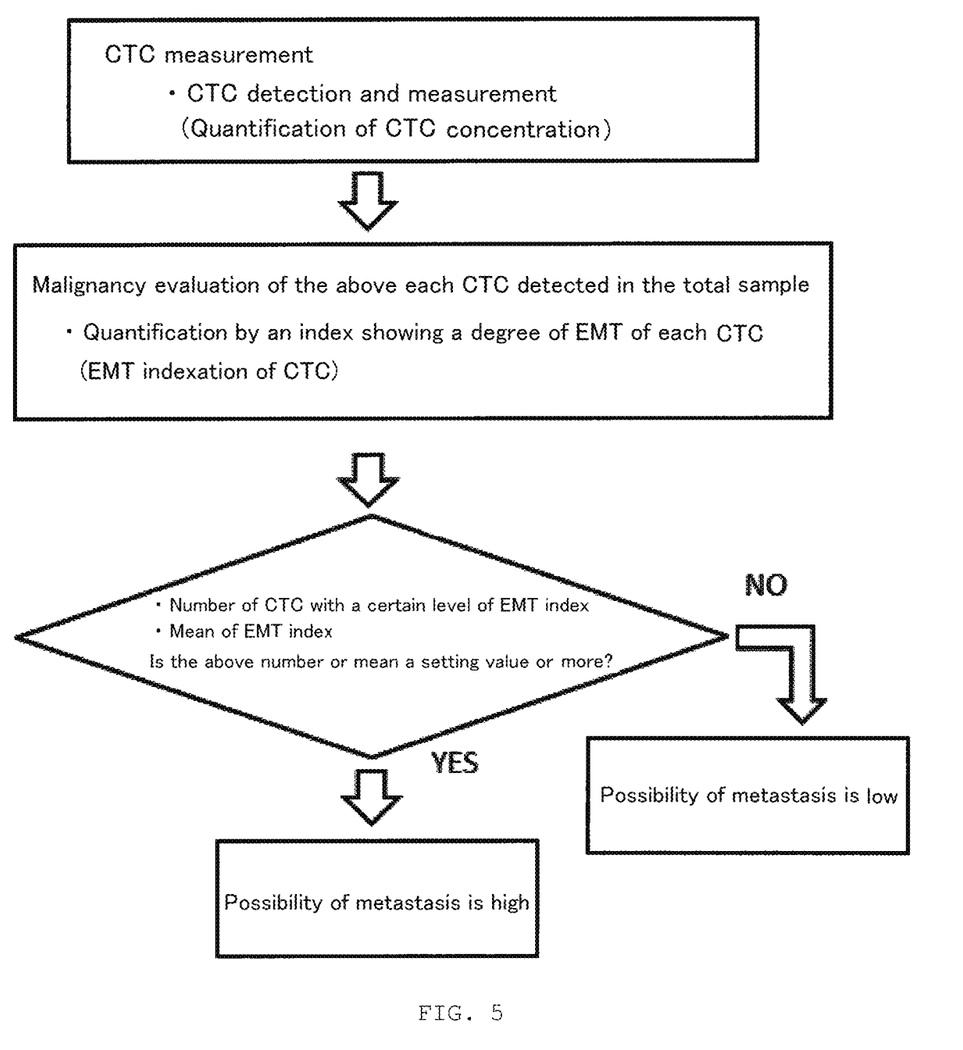
FIG. 5 is a view showing an example of applying an evaluation result of EMT index to a diagnosis of the possibility of metastasis of cancer.

As shown in FIG. 4, the detection rates of KATO-III cells, A549 cells, PC-9 cells, and PC-14 cells were approximately 100%, 89%, 75%, and 100%, respectively.

The detection rate of PC-14 cells in which EpCAM was not expressed, was 100%. Therefore, it was revealed that the detection method of the present invention can effectively detect CTCs of metastatic cancer in which the EMT was induced.

Finally, a characteristic feature of the present invention is shown from the other point of view.

In the apparatus measuring the fluorescence signal intensity of each of the cells, an analog value showing a cell characteristic feature (degree of EMT of CTC in the present invention), which is defined by multiple signal intensities and an apparatus constant, was calculated, and an evaluation of the analog value corrected by the apparatus constant was achieved. That is to say, the measurement data of each of the cells between various apparatuses can be compared. In other words, the analog information of each of the cells can be used on medical diagnosis in the method of the present invention. In the conventional flow cytometer, numbers of cells detected in a certain range of signal intensity are used as information for diagnosis. The conventional information is not the analog information of each of the cells, but merely the numbers of detected cells. That is, it is impossible to express the analog value showing a characteristic feature of each of the cells in the conventional flow cytometer. In other words, according to the present invention, the analog value of each of the cells present in the samples of the patients can be used for medical diagnosis.

INDUSTRIAL APPLICABILITY

The present invention has advantages in that (1) CTCs are detected by only a blood drawing from patients so that cancer can be found. Further, the present invention has advantages in that (2) in the patients wherein the cancer tissue was removed by surgery, a recurrence can be found early by only a blood drawing after surgery.

Although the present invention has been described with reference to specific embodiments, various changes and modifications obvious to those skilled in the art are possible without departing from the scope of the appended claims.

The invention claimed is:

1. An apparatus for detecting of the degree of malignancy of circulating tumor cells comprising:
    (a) a means of receiving an amount of fluorescence signal or luminescence signal of epithelial cell-binding component bound to each of the circulating tumor cells (E) and an amount of fluorescence signal or luminescence signal of mesenchymal cell-binding component bound to each of circulating tumor cells (M), wherein E is distinguishable from M, and
    (b) a means of determining the degree of epithelial-mesenchymal transition of each of the circulating tumor cells by calculating a ratio between the received amount of signal of the epithelial cell-binding component (E) and the received amount of signal of the mesenchymal cell-binding component (M).

2. The apparatus for detecting of the degree of malignancy of circulating tumor cells (P) according to claim 1, wherein the degree of epithelial-mesenchymal transition in the means (b) is represented by a formula selected from a group consisting of formula (1)

$$P = M/(E+M) \tag{1},$$

formula (2)

$$P = E/(E+M) \tag{2},$$

formula (3)

$$P = \text{Log}[M/(E+M)] \tag{3, and}$$

formula (4)

$$P = \text{Log}[E/(E+M)] \tag{4}.$$

3. The apparatus for detecting of the degree of malignancy of circulating tumor cells according to claim 1, wherein the epithelial cell-binding component is an antibody specifically binding to cytokeratin, Epithelial cell adhesion molecule, or E-cadherin, and the mesenchymal cell-binding component is an antibody specifically binding to vimentin, or N-cadherin.

4. The apparatus for detecting of the degree of malignancy of the circulating tumor cells according to claim 1, further comprising
    (c) a means of setting a reference of state before an onset of epithelial-mesenchymal transition (0) and a reference of state after a termination of epithelial-mesenchymal transition (1) by measuring particles to which a fluorescence substance labeling the epithelial cell-binding component is bound, as the reference of state before an onset of epithelial-mesenchymal transition (0), and measuring particles to which a fluorescence substance labeling the mesenchymal cell-binding component is bound, as the reference of state after a termination of epithelial-mesenchymal transition (1).

5. The apparatus for detecting of the degree of malignancy of the circulating tumor cells according to claim 1, further comprising
   (d) a means of displaying the degree of epithelial-mesenchymal transition of each of the circulating tumor cells.

* * * * *